United States Patent
Williams

(10) Patent No.: US 6,248,274 B1
(45) Date of Patent: Jun. 19, 2001

(54) METHOD OF MANUFACTURING A CATAMENIAL/TAMPON DEVICE

(75) Inventor: Karla E. Williams, Emerson, NJ (US)

(73) Assignee: Playtex Products, Inc., Westport, CT (US)

(*) Notice: Subject to any disclaimer, the term of this patent is extended or adjusted under 35 U.S.C. 154(b) by 0 days.

(21) Appl. No.: 09/399,654

(22) Filed: Sep. 21, 1999

(51) Int. Cl.⁷ .................. D01D 5/06; D01F 2/10
(52) U.S. Cl. .................. 264/103; 264/188; 264/211
(58) Field of Search .................. 264/103, 188, 264/211

(56) References Cited

U.S. PATENT DOCUMENTS

| | | |
|---|---|---|
| 3,222,857 | 12/1965 | Keyser . |
| 3,339,357 | 9/1967 | Marzocchi et al. . |
| 3,474,616 | 10/1969 | Zeisberg . |
| 3,479,811 | 11/1969 | Walters . |
| 4,525,410 | 6/1985 | Hagiwara et al. . |
| 4,744,374 | 5/1988 | Deffeves et al. . |
| 4,826,497 * | 5/1989 | Marcus et al. .................. 604/359 |
| 4,911,898 | 3/1990 | Hagiwara et al. . |
| 4,911,899 | 3/1990 | Hagiwara et al. . |
| 5,364,380 | 11/1994 | Tanzer et al. . |
| 5,413,747 * | 5/1995 | Akers et al. .................. 264/211 |
| 5,428,948 | 7/1995 | Ballhausen et al. . |
| 5,457,950 | 10/1995 | Ballhausen et al. . |
| 5,460,881 | 10/1995 | Hsu . |
| 5,489,469 | 2/1996 | Kobayashi et al. . |
| 5,492,759 | 2/1996 | Eriksson et al. . |

* cited by examiner

Primary Examiner—Leo B. Tentoni
(74) Attorney, Agent, or Firm—Ohlandt, Greeley, Ruggiero, & Perle, LLP

(57) ABSTRACT

A method of manufacturing a catamenial/tampon device according to which the benefit of incorporating the desired odor adsorbent material in the first instance directly into the fibers as they are formed or spun results in eliminating the potential for dusting during processing of the device and the need for binders and/or thickening agents normally used.

7 Claims, 1 Drawing Sheet

METHOD OF MANUFACTURING A CATAMENIAL/TAMPON DEVICE

BACKGROUND OF THE INVENTION

1. Field of the Invention

This invention relates to a method of manufacturing catamenial and tampon devices and, in particular, to a method which completely simplifies the conventional way of making an odor absorbent tampon; for example, by eliminating the additional processing steps normally employed.

2. Description of the Prior Art

Applicants assignee, as well as a number of other makers of catamenial or tampon devices, currently market such devices which achieve odor adsorbency in non-deodorant catamenials or tampons. However, such adsorbency is typically provided by a strip comprising an odor adsorbing material adhered to a non-woven material with an acrylic binder. The odor adsorbent strip is fed into the tampon forming machine along with rayon pads. The pads and strip are then formed into the tampon pledget. Alternately, the odor adsorbing material is mixed with water (a suspension aid, e.g., Veegum may be used) and added as a slurry directly to the rayon pads prior to their formation into the tampon pledget.

It will be manifest to those skilled in this art that the addition of the odor adsorbent strip, as described, is costly. A less costly alternative to the addition of a strip is to apply the odor adsorbent material, for example, as a powder or in a slurry, directly to the tampon. However, this and similar lower cost alternatives are technically more difficult since they involve additional steps in the tampon forming process and have the potential for leaving residue that would accumulate on the tampon forming equipment.

What has been discovered or recognized is that the technically difficult and problematic techniques, which are currently followed as possible alternatives for the addition of the odor adsorbent strip, can be side-stepped or avoided by adopting a more efficient method.

As background for an understanding and appreciation of the present invention, reference may be made to the following U.S. Pat. Nos.: 3,222,857, 3,339,357, 3,479,811, and 5,460,881. Although these relate in general to process and apparatus for producing impregnated fiber materials of one kind or another, they fail to recognize what is inherent in the concept of the present invention: that a significant advantage is obtained by uniquely combining with the usual steps involved in producing a catamenial/tampon device, the step—at the beginning of the process—of embedding the odor adsorbent material in the matrix fibers while these fibers are being formed or processed; in other words, at a time prior to the actual formation or fabrication of the tampon pledget.

A substantial benefit which results from the unique step described is that there is uniform distribution of the adsorbent within the finished catamenial/tampon product. This result contrasts sharply with that obtained by use of conventional processes.

SUMMARY OF THE INVENTION

It is an object of the present invention to entirely simplify the process or method of making an odor adsorbent tampon, such object being achieved by incorporating the odor adsorbent material directly into the fibers involved during the process of forming such fibers, which fibers are subsequently used in the construction of a catamenial/tampon device.

The fundamental features of the present invention reside in a method of manufacturing the aforenoted catamenial/tampon device and the product produced by that method. The method, briefly stated, includes the steps of forming a plurality of fibers, preferably by extrusion, and impregnating the fibers with finely divided odor adsorbent material while the process of forming the fibers is being performed. Thereafter, the plurality of fibers so formed are suitably and conventionally brought together to produce the finished device.

Other and further objects, advantages and features of the present invention will be understood by reference to the following specification in conjunction with the annexed drawings, wherein like parts have been given like numbers.

DESCRIPTION OF THE INVENTION

Figure 1:
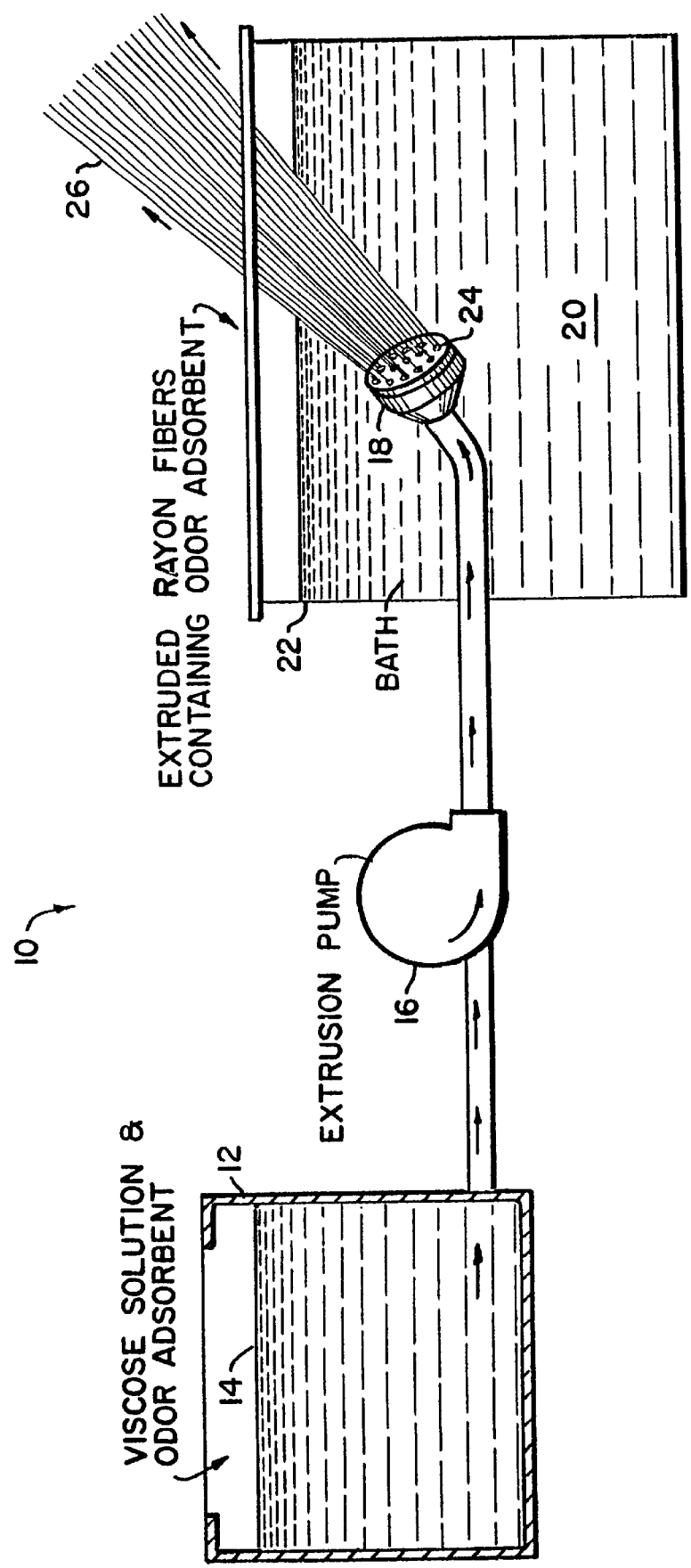
FIG. 1 is a perspective view of the apparatus deployed in the practice of the invention.

Referring to the drawing and, there will be seen a preferred arrangement for practicing the method of the present invention, particularly, illustrating the novel process by which fibers for use in tampons are impregnated, as they are being generated, with odor adsorbent material, rather than having the pledget or the like formed from them impregnated at a later stage of manufacturing.

Shown in FIG. 1 is an apparatus generally represented by reference numeral 10 by which the basic objective of the present invention is realized. Seen on the left is a tank or vessel 12 containing a viscose solution 14 to which a finely divided odor adsorbent has been added. The solution is pumped by means of an extrusion pump 16 connected to an apertured extrusion device 18 which is disposed in an acid bath 20 contained in tank 22.

Operation of the extrusion pump 16 produced sufficient pressure to force the viscose solution 14 or the like through apparatus 24 and into the acid bath 20, thereby providing individual rayon fibers 26 that can be further conventionally processed to produce the catamenial product.

The odor adsorbent material would be any of the various known odor adsorbent materials. However, research has indicated that for use in a menstrual tampon/catamenial device where moisture will be present, certain materials are more effective in adsorbing odor. Zeolites (particularly clinoptilolite and chabasite, both available from GSA Resources, Tucson, Ariz. and identified as ZK-406H and ZS500A, respectively) have been found to be uniquely effective for this application.

From the description herewith provided of the present invention, it will be understood that the great advantage and benefit of incorporating the odor adsorbent material in the first instance directly into the fibers eliminates both the potential for dusting during processing of catamenial devices and the need for binders and/or thickening agents that are normally used in the conventional methods. As previously noted, the method has been made more effective because the impregnation step normally performed at the end stage of the manufacturing procedures has already been accomplished, thereby eliminating the residue accumulation problem previously discussed.

The final step in the method of the present invention is a conventional step of bringing together a plurality of the individual fibers 26 formed and treated as described, so as to produce the finished product. Thus the already impregnated fibers, whether they be of rayon or other materials, are brought together as rayon and/or cotton fiber have conventionally been brought together in known tampons and in other catamenial devices. This bringing together can be accomplished by conventional non-weaving techniques.

Although in this description of the method of the present invention, a preferred embodiment thereof has been specifically illustrated, it will be appreciated that alternate techniques may be exploited for achieving the essential objective of incorporating the odor adsorbent material within the fibers while such fibers are being formed or processed.

The present invention having been thus described with particular reference to the preferred forms thereof, it will be obvious that various changes and modifications may be made therein without departing from the spirit and scope of the invention as defined in the appended claims.

What is claimed is:

1. A method of manufacturing a catamenial/tampon product comprising:

(1) forming a plurality of fibers from a viscose solution; and, during the process of forming, incorporating a finely divided odor adsorbent material within the fibers; and (2) bringing together the plurality of fibers so as to form the finished catamenial/tampon product.

2. The method as defined in claim 1, including the steps of adding an odor adsorbent material to the viscoe solution prior to extrusion of the viscose solution.

3. The method as defined in claim 2, including the step of pumping the viscose solution containing the odor adsorbent material to a device for extruding the fibers, whereby the odor adsorbent material is incorporated within the fibers.

4. The method as defined in claim 1, wherein the fibers are rayon.

5. The method as defined in claim 4, wherein the odor adsorbent material is zeolite.

6. The method as defined in claim 5, wherein the zeolite is the species clinoptilolite.

7. The method as defined in claim 5, wherein the zeolite is the species chabasite.

* * * * *